(12) United States Patent
Kleinberg et al.

(10) Patent No.: US 6,524,558 B2
(45) Date of Patent: *Feb. 25, 2003

(54) DENTAL ANTI-HYPERSENSITIVITY COMPOSITION AND METHOD

(75) Inventors: Israel Kleinberg, Smithtown, NY (US); Ana Marie Acevedo, Caracas (VE); Robi Chatterjee, Centereach, NY (US)

(73) Assignee: The Research Foundation of the State University of New York, Stony Brook, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/940,723

(22) Filed: Aug. 27, 2001

(65) Prior Publication Data

US 2002/0064504 A1 May 30, 2002

Related U.S. Application Data

(63) Continuation of application No. 09/504,264, filed on Feb. 15, 2000, now Pat. No. 6,436,370
(60) Provisional application No. 60/140,560, filed on Jun. 23, 1999.

(51) Int. Cl.[7] ............................. A61K 7/16; A61K 33/10
(52) U.S. Cl. ......................... 424/49; 424/49; 424/687; 514/835
(58) Field of Search .................... 424/49, 687; 514/835

(56) References Cited

U.S. PATENT DOCUMENTS

| 3,932,608 A | 1/1976 | Anderson et al. ............. 424/54 |
| 3,943,241 A | 3/1976 | Anderson et al. ............. 424/54 |
| 4,064,138 A | 12/1977 | Saari et al. .................. 548/344 |
| 5,762,911 A | 6/1998 | Kleinberg et al. ............ 424/49 |

FOREIGN PATENT DOCUMENTS

| EP | 0 569 666 A2 | 11/1993 |
| GB | 2055574 | 3/1981 |
| JP | 61 233 612 | 10/1986 |
| WO | 0 711543 A1 | 5/1996 |
| WO | 97/32565 | 9/1997 |

OTHER PUBLICATIONS

US 5,989,525, 11/1999, Kleinberg et al. (withdrawn)
Supplementary European Search Report for Application EP97917135; Aug. 25, 1999.
Chemical Abstracts vol. 106, No. 10, Mar. 9, 1987 Abstract No. 72737a Tsujita Satoshi et al. "Chewing Gums Containing Phytic Acid Derivatives for Dental Plaque Prevention" XP002113030.
Patent abstract of Japan, Publication No. 07258053, Publication date Sep. 10, 1995.

*Primary Examiner*—Frederick Krass
*Assistant Examiner*—Donna Jagoe
(74) *Attorney, Agent, or Firm*—Darby & Darby

(57) ABSTRACT

The present invention relates to compositions and methods for calcifying dental tissue, e.g., preventing or treating dental hypersensitivity. An oral composition of arginine bicarbonate and calcium carbonate promotes the formation of dentinal tubule plugs aided by combining calcium and phosphate in the fluid. In a specific example, an arginine bicarbonate/calcium carbonate mixture blocked dentinal tubules in a model system. In addition to treating dentinal sensitivity, the compositions and methods of the invention provide for calcifying exposed tooth pulp, calcifying the base or all of a pit or fissure in a tooth, and treating a carious lesion.

16 Claims, 7 Drawing Sheets

DENTAL ANTI-HYPERSENSITIVITY COMPOSITION AND METHOD

This is a continuation of U.S. patent application Ser. No. 09/504,264, now U.S. Pat. No. 6,436,370, filed Feb. 15, 2000 which claims priority of U.S. Provisional Application No. 60/140,560, filed Jun. 23, 1999, each of which are incorporated herein by reference, in their entireties.

FIELD OF THE INVENTION

The present invention relates to compositions and methods for preventing or treating dental hypersensitivity.

BACKGROUND OF THE INVENTION

The three mineralized tissues of teeth are enamel, cementum and dentine. In human teeth, enamel covers the crown dentine whereas cementum covers the root dentine. In turn, the dentine encloses the pulp of the tooth which provides the dentine with vascular and neural support. Unlike enamel and cementum, the dentine is transversed by numerous tubules. The tubule walls are comprised of the calcified matrix of the dentine and the tubule space is filled with fluid (dentinal fluid) derived from pulp tissue fluid and serum. The matrix mineral is comprised mainly of the calcium phosphate salt, hydroxyapatite, which is poorly soluble at neutral and alkaline pH, and progressively more soluble as the pH becomes progressively more acidic.

Because of their rigid walls, the fluid that fills the narrow dentinal tubules enables cold, tactile, evaporative and osmotic stimuli to be transmitted through the dentine to the pulp in the form of fluid movement. This movement of dentinal fluid is sensed as sharp pain of short duration. This pain is elicited when the odontoblasts that protrude into the pulpal ends of the tubules are disturbed and as a result, the mechano-receptors of the pulpal nerve fibers attached thereto are stimulated. The neural response is usually referred to as dentinal pain and the involved dentine as hypersensitive dentine.

Dentinal hypersensitivity results when protective enamel or cementum covering dentine is lost. Cementum is easier to breach than enamel, because cementum is thinner and more easily eroded by acids. However, breach of cementum cannot happen until there is gingival recession and exposure of the root surface to the oral milieu. Individuals with breached cementum and suffering with dentinal hypersensitivity often experience pain when the exposed area of the tooth comes into contact with cold air or hot and cold liquids or foods that are sweet or acidic or is touched with a metal object.

One way that loss of cementum occurs (and the same is true of enamel) is by the process of dental caries. Acids are produced as end-products of the bacterial degradation of fermentable carbohydrate and these acids dissolve hydroxyapatite, which, like dentine and enamel, is the main calcium phosphate mineral that comprises most of the mineral of the cementum. Another source is acidic foods which, if ingested frequently and for prolonged periods of time, will cause tooth demineralization. These include fruit juices and many beverages, both alcoholic and non-alcoholic. Other acidic agents leading to chemical erosion include various oral personal care products. Amongst these are many of the commercially available mouthwashes and some toothpastes. Abrasive toothpastes and vigorous brushing can aid the erosion process. Another way in which dentinal tubules lose their protective cementum and enamel coverings is through procedures performed by the dentist or hygienist in the dental office. This includes cavity and crown preparation of teeth for fillings and other restorations. It also includes cementum removal during scaling and root planing by the periodontist or dental hygienist.

Many attempts have been made with limited success to plug exposed dentinal tubules and to thereby reduce or stop the ability of stimuli to reach the pulp and cause pain. Materials either singly or in combination have been tried to produce an effective plug. Blockage of the tubules through the formation of a calcium phosphate precipitate is a common approach. This includes the mixing of a soluble calcium salt with a soluble phosphate salt and immediately applying the combination to the open tubules. Alternatively, application of one salt before the other to try to get a precipitate to form within tubules is also used.

Substances other than calcium phosphate have also been utilized. For example, U.S. Pat. No. 3,683,006 to Hodosh describes using potassium, lithium or sodium nitrate. Another example is calcium oxalate particles of small and large size. Application of a protein denaturing agent, such as an alcohol, a surfactant, or a chaotropic salt, can also plug an exposed dentinal tubule since there is protein material within the dentinal tubules and denaturation can sometimes result in partial or complete tubule plugging. Still another but more drastic approach is to place a dental restoration in the affected area or cover the area with an adhesive material. For example, U.S. Pat. No. 5,139,768 to Friedman describes using a varnish containing strontium salt in a sustained hydrophobic polymer. Adherence without leakage of fluid from the tubules is not always easy to accomplish because adherence to a wet surface is difficult to achieve considering that the continual outward flow or leakage of dentinal fluid from the tubules while a filling or adhesive is setting is hard to stop.

Attempts to treat tooth sensitivity other than by plugging have involved depolarization of the nerve fiber membranes essential for nerve impulse transmission. Potassium salts, especially potassium nitrate, have been largely used for this purpose. For example, U.S. Pat. Nos. 4,751,072 and 4,631,185 to Kim describe using potassium bicarbonate and potassium chloride.

Thus, there remains acute need in the art for compositions and methods for blocking exposed dentinal tubules to treat dentinal hypersensitivity.

There is a further need in the art to identify compositions and methods that can achieve intrinsic blockage of dentinal tubules, e.g., by taking advantage of the presence of calcium and phosphate ions in dentinal fluid, which potentiates their ability to precipitate as a calcium phosphate salt and achieve tubule blockage.

The present invention advantageously provides such compositions and methods.

SUMMARY OF THE INVENTION

The present invention advantageously provides an oral composition comprising a guanidinium alkaline salt and a calcium salt and an orally acceptable carrier, wherein the pH of the composition ranges from about 7.5 to about 9.5, and the calcium salt is poorly soluble in water. In a more specific embodiment, the oral composition consists essentially of the guanidinium alkaline salt and poorly soluble calcium salt with an orally acceptable carrier. In yet a further embodiment, the oral composition substantially lacks any phytates. Preferably, the guanidinium is arginine and the calcium salt is calcium carbonate.

The invention further provides a powder composition comprising, or more particularly consisting essentially of, an arginine salt (or equivalent guanidinium salt) and calcium carbonate (or an equivalent poorly soluble calcium salt). Such a powder composition, when in contact with a calcium phosphate solution or slurry, or a body fluid (e.g., dentinal fluid, saliva, or pulpal fluid), body cells, or body tissues (e.g., dental pulp), yields a pH ranging from about 7.5 to about 9.5. Preferably, the powder composition lacks phytates.

In a further aspect, the invention provides a pulpal calcification filling comprising, or more particularly consisting essentially of, an arginine salt (or an equivalent guanidinium salt) and calcium carbonate (or an equivalent poorly soluble calcium salt) and a filling carrier, wherein the pH of the composition ranges from about 7.5 to about 9.5.

The invention further provides methods for treating or preventing dentinal sensitivity, plugging tubules, treating a carious lesion, calcifying an exposed tooth pulp, and calcifying the base or all of a pit or fissure in a tooth. The methods comprise administering a composition comprising, or more particularly consisting essentially of, an arginine (or equivalent guanidinium) salt and calcium carbonate (or an equivalent poorly soluble calcium salt), wherein a pH of the composition ranges from about 7.5 to about 9.5, to the affected area.

Thus, it is an object of the invention to provide a composition suitable to calcify dental lesions.

The invention has as a further object a composition for reducing dentinal sensitivity.

Another object of the invention is to provide methods for calcifying dental lesions, including dentinal tubules, exposed tooth pulp, carious lesions, and pits or fissures.

These and other objects of the invention have been achieved as further elaborated in the accompanying Drawings, Detailed Description of the Invention, and Examples.

DETAILED DESCRIPTION OF THE INVENTION

Figure 1:
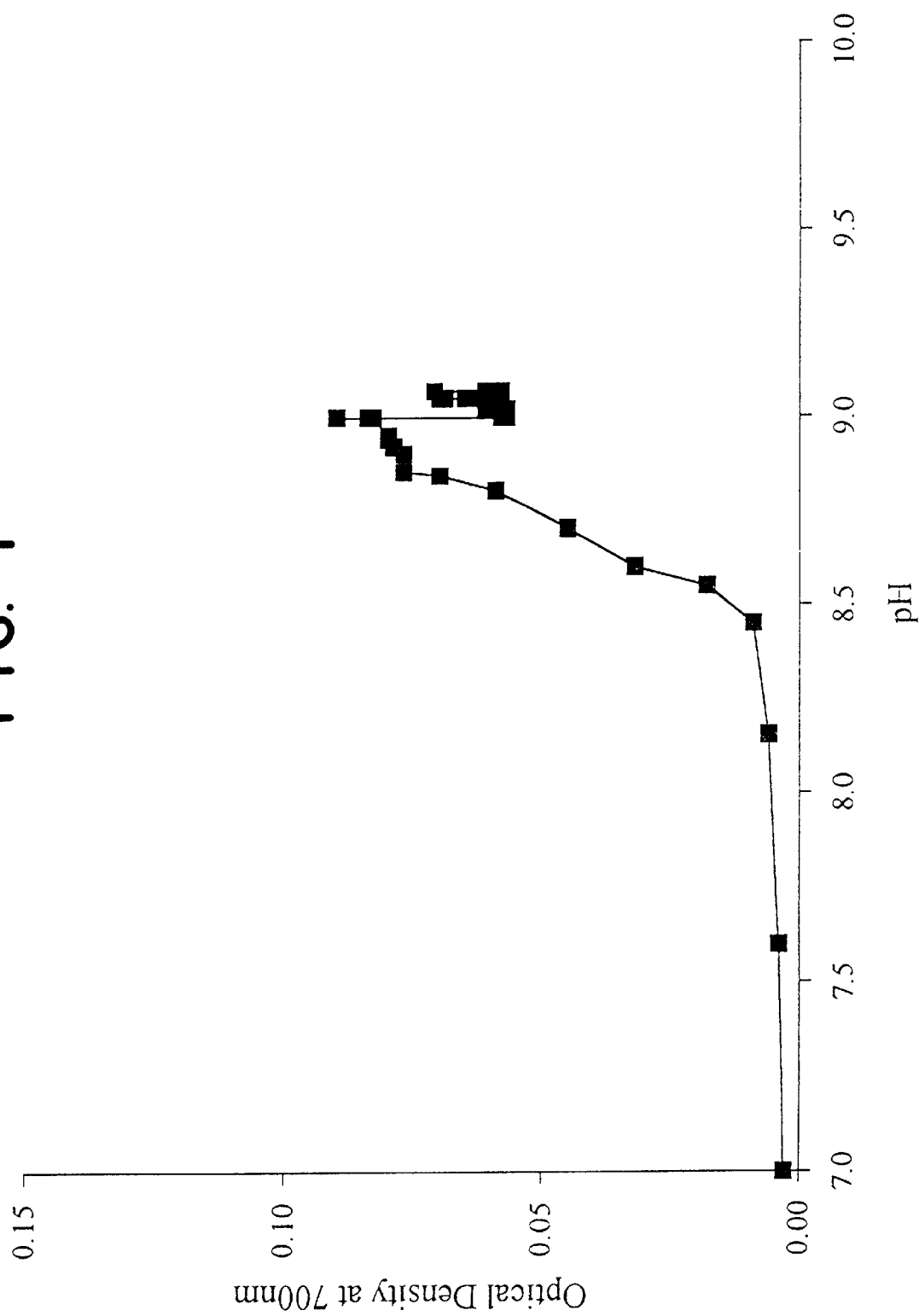
FIG. 1. Titration of artificial dentinal fluid with arginine bicarbonate ($ArgHCO_3$) solution.

The present invention has identified an oral composition unlike the oral compositions previously identified, capable of reducing or preventing dentinal hypersensitivity. It has been discovered by the present invention that an oral composition containing, and preferably consisting essentially of, arginine bicarbonate (or equivalents thereof) and calcium carbonate (or equivalents thereof) promotes the formation of dentinal tubule plugs aided by combining calcium and phosphate in the fluid. It has also been discovered by the present invention that an oral composition containing arginine bicarbonate and calcium carbonate promotes the formation of salivary precipitin, a carbohydrate-protein-calcium phosphate complex present primarily in dental plaque, which is formed from saliva when salivary proteins combine with calcium and phosphate, to reduce or prevent dentinal hypersensitivity.

Arginine bicarbonate and calcium carbonate are the preferred components of compositions of the invention. However, compounds with equivalent or closely related properties can substitute for arginine bicarbonate. Other arginine compounds that can be used include, but are not limited to, arginine hydroxide, arginine carbonate, arginine phosphate, and arginine organic phosphate. Although arginine phytate may be used, preferably it is avoided except at high pH. Arginine bicarbonate is a guanidinium alkaline carbonate salt; other such salts may be used in its place. Examples include aminoguanidine and aminoguanidinium analogues.

Also, calcium compounds with equivalent or closely related solubilities can substitute for calcium carbonate or part of it. These include monocalcium phosphate, dicalcium phosphate, tricalcium phosphate, calcium fluoride, calcium monofluorophosphate, sodium calcium pyrophosphate, calcium laurate, and calcium palmitate.

Thus, the present invention relates to a method of reducing or preventing tooth hypersensitivity by delivering into the oral cavity an oral composition containing a therapeutically effective amount of arginine bicarbonate and calcium carbonate distributed in an oral vehicle. The amount of arginine bicarbonate and calcium carbonate sufficient to reduce or prevent dentinal hypersensitivity is an amount sufficient to promote dentinal plugging. It has been discovered that arginine bicarbonate and calcium carbonate promote the formation of and provide particles in the oral cavity for plugging the dentinal tubules of teeth. By plugging the dentinal tubules, the oral compositions used in the method of this invention are capable of reducing dentinal hypersensitivity. A mixture of arginine bicarbonate, which is highly soluble, with poorly soluble calcium carbonate (or calcium phosphate) yields a composition that gives a pH of about 8.0 to 9.0, which is ideal for tubule plugging. Calcium carbonate is a poorly soluble calcium salt which is defined here as one having a solubility of about 0.1 to about 100 mg in 100 ml of water at room temperature near or above a pH of about 5, and especially above neutral pH.

Arginine bicarbonate and calcium carbonate are well suited for promoting dentinal plugging for a number of reasons. For one thing, they are effective neutralizers of acid especially since they can lose carbon dioxide and produce arginine hydroxide (arginine free base) and calcium hydroxide, respectively, when they come in contact with acid; this and being alkaline salts results in a rapid and substantial rise in the pH that is particularly favorable to deposit formation.

A second reason is that calcium carbonate is poorly soluble above neutrality but is progressively more soluble as the pH becomes acidic. This behavior is similar to that of the calcium phosphate in tooth mineral tissues, thereby enabling the calcium carbonate to provide a renewable reservoir of calcium to reduce or prevent erosion of the cementum and dentine.

A third reason is that arginine bicarbonate surprisingly has adhesive properties particularly useful at a pH ranging from about 7.5 to about 9.5, and preferably 8 to about 9 or 9.5. Together with the poor solubility of calcium carbonate or a like calcium salt, the arginine bicarbonate combination favors plugging of open dentinal tubules by binding of calcium carbonate particles and their attachment to the tubule walls and tooth surface. Demonstration of plugging effectiveness in an actual dentine plugging model shows the arginine bicarbonate/calcium carbonate combination is significantly superior. This means of plugging tubules is different from the prior art, where formation of tubule plugs is attempted by producing calcium phosphate precipitates from acidic solutions of moderately to highly soluble calcium and phosphate salt solutions or the like.

Dentinal sensitivity resulting from the acids generated by bacteria is really an early stage in the development of a dental caries lesion. The bacteria found at the distal ends of tubules exposed to the oral environment are the same as those found in dental plaque.

Consequently, the preferred bicarbonate cation is arginine since it will favor the base forming metabolism and the growth of arginolytic rather than non-arginolytic bacteria. The former are more alkalogenic and less cariogenic than the non-arginolytic bacteria. This additional factor will ensure sustenance of an elevated pH and a reservoir of alkali generation capability within and in association with the dentinal tubules.

The preferred composition of arginine bicarbonate combined with calcium carbonate has a number of effects. It neutralizes any acid in the tubules, ensures a pH above neutrality and as high as, and in a specific embodiment greater than, about 9.0, provides needed calcium ions, provides a poorly soluble salt that has a small particle size to facilitate filling and plugging the dentinal tubules, and provides arginine to favor growth of and alkali production by alkalogenic bacteria for maintenance of an alkaline pH. Moreover and most importantly, arginine bicarbonate in the preferred pH range of use has been found unexpectedly to have adhesive properties that favor tubule plugging, an important property in light of the fact that in vivo flow of dentinal fluid out of the dentinal tubules under pressure makes any plugging difficult.

As used herein, the terms "about" and "approximately" mean within 20%, preferably within 10%, and more preferably within 5% of a given value, unless another definition is provided.

Compositions

The present invention provides an oral composition containing therapeutic amounts of arginine bicarbonate and calcium carbonate distributed in an acceptable oral vehicle. The oral compositions of this invention by weight may contain, for example, arginine bicarbonate in a concentration ranging from about 1 to about 25% and calcium carbonate in a concentration ranging from about 5 to about 50%. In one embodiment, the oral composition further contains a therapeutically effective amount of fluoride, for example, 10 to 1500 ppm. Any conventional ingredients for the particular oral vehicle may further be added to the oral compositions of the present invention.

The pH of the oral compositions of the present invention generally ranges from about 7.5 to about 9.5, preferably from about 8.0 to about 9.0, where arginine bicarbonate exhibits adhesive properties. The pH of the oral compositions described herein can be lowered with arginine bicarbonate or acid such as hydrochloric, or raised with arginine hydroxide (arginine free base) or bases such as sodium hydroxide or buffering agents such as sodium bicarbonate. In addition to arginine bicarbonate and calcium carbonate, the oral compositions of this invention may contain any conventional ingredient for the particular oral vehicle discussed herein.

The amount of calcium carbonate and arginine bicarbonate sufficient to reduce or prevent dentinal hypersensitivity varies with the type of oral vehicle used to deliver the therapeutic agent. Generally, the oral vehicles described by the present invention contain between approximately 5 grams to 50 grams of calcium carbonate and between approximately 1 gram to 25 grams of arginine bicarbonate per 100 grams oral composition. In a further embodiment of the present invention, the oral compositions used in the method of this invention contain a therapeutically effective amount of fluoride. The concentration of fluoride generally ranges from approximately 10 to 1500 ppm. Calcium fluoride is a preferred form of fluoride because it can be incorporated into a tubule plug along with calcium carbonate largely as particles, where fluoride ions along with calcium ions can be slowly released over prolonged periods of time. Despite its low solubility, calcium fluoride provides a source of calcium and fluoride ions and the ability to develop a less acid soluble tubule plug than if absent.

Acceptable oral vehicles include any conventional oral delivery system, such as dental care products, food products, and chewing gum. Examples of dental care products include, for example, dentifrices, topical solutions or pastes, mouthwashes in the form of liquids or sprays or slurries, powders, gels or tablets, and dental flosses. Examples of food products which may contain oral compositions described herein include, for example, lozenges and confections.

In addition to arginine bicarbonate and calcium carbonate, the oral compositions described in accordance with the present invention may contain any conventional ingredient for the particular oral vehicle. For example, liquid mouthwashes may contain solvents such as distilled or deionized water and ethanol; a sweetening agent such as saccharine, aspartame, sorbitol, mannitol, and xylitol; and a flavoring agent such as peppermint oil and spearmint oil (see U.S. Pat. Nos. 4,226,851 and 4,606,912). Dentifrices may contain, for example, a conventional abrasive such as resins, silica, and insoluble alkali metal metaphosphates in a standard amount of about 20% to about 60% by weight; a binder such as hydroxyethylcellulose, xanthin gum, and sodium carboxymethylcellulose in a standard amount ranging from about 0.5% to about 5.0% by weight; a foaming agent such as sodium lauryl sulfate, sodium coconut monoglyceride sulfonate, and sodium-N-methyl-N-palmitoyl taurine in a standard amount ranging from about 0.5% to about 3.0% by weight; a flavoring agent; a sweetening agent; an antiseptic agent and any other ingredient required for the particular composition as recognized by those skilled in the art (see U.S. Pat. Nos. 4,177,258 and 4,721,614). Tablets and powders may contain, for example, a vehicle such as lactose and mannitol, a binder such as corn starch and carboxymethylcellulose, and a disintegrator.

A dentifrice or paste for localized application to a sensitive tooth site such as breeched cementum of an orally exposed root surface may be one that is simpler in composition and applied with a soft applicator. Such a dentifrice or paste may or may not contain conventional abrasive, foaming agent, and flavoring agents. Localized sites such as the dentine following tooth preparation for a dental restoration would also involve simpler compositions and include fillers used in dental pulp cappings, cavity liners and cements and any other ingredients required for the composition by those skilled in the art (Craig et al., 1989, Restorative Dental Materials. Mosby, St. Louis, pp. 189–225). For example, zinc oxide and eugenol at levels of (20 and 25%, respectively) would be appropriate for dental cement compositions.

The oral compositions described herein may be produced by adding arginine bicarbonate having a concentration by weight ranging from about 1 to about 25% and calcium carbonate having a concentration by weight ranging from about 5 to about 50% to an acceptable oral vehicle using conventional techniques. The pH of the composition may range from approximately 7.5 to approximately 9.5, preferably approximately 8.0 to approximately 9.0. The amount of arginine bicarbonate and calcium carbonate to retard or prevent dentinal hypersensitivity is an amount sufficient to plug the exposed dentinal tubules in teeth in the oral cavity by promoting the formation of dentinal plugs. For example, a dentifrice or paste may contain arginine bicarbonate and calcium carbonate in a concentration ranging from about 1 to about 25% and about 5 to about 50%, respectively. A mouthwash or slurry may also contain arginine bicarbonate and calcium carbonate in a concentration ranging from about 1 to about 25% and about 5 to about 50%, respectively.

The present invention further provides an article of manufacture comprising a packaging material and the oral compositions described herein contained within said packaging material, wherein said oral composition is effective in retarding or preventing dentinal hypersensitivity and wherein said packaging material contains a label that indicates that said oral composition is effective in retarding or preventing dentinal hypersensitivity. The packaging material used to contain the oral compositions can comprise glass, plastic, metal or any other suitably inert material. For example, dentifrice containing the oral composition of the present invention may be contained in a collapsible tube, typically aluminum, line lead or plastic or a squeeze pump or pressurized dispenser to measure out the contents or in a tearable sachet.

The oral composition of the present invention may also be used in a prophylaxis paste for polishing teeth or treating sensitive teeth or preventing the development of sensitive teeth after scaling, root planing or stain removal by a dentist or hygienist, in a small dental container, such as a tub of a size that permits easy access of the rotary attachments used in dental offices on dental hand-pieces.

Methods

The present invention is directed to a method for promoting the formation of dentinal tubule plugs by delivering into the oral cavity an oral composition containing arginine bicarbonate and calcium carbonate. The present invention is further directed to a method for promoting the formation of salivary precipitin in the oral cavity by delivering into the oral cavity an oral composition containing arginine bicarbonate and calcium carbonate. In addition to arginine bicarbonate and calcium carbonate, the oral compositions used in this method may contain any conventional ingredient for the particular oral vehicle as outlined above. In another embodiment of this invention, the oral compositions used in this method contain a therapeutically effective amount of fluoride, generally between about 10 to about 1500 ppm. In one embodiment, the oral compositions contain arginine bicarbonate in an amount ranging from about 1 to about 25% and calcium carbonate in the amount ranging from about 5 to about 50%, Related Uses of Compositions of the Invention In related applications, tubule plugging with arginine bicarbonate/calcium carbonate to stop dentinal fluid flow is desirable to enable proper placement of a non-leaking cavity liner, dental filling, or crown. Wetness, because of leakage of dentinal fluid, will often result in poor sealing of these devices or appliances. This is why sensitivity often persists and does so until natural tubule plugging or tooth pathology and demise occurs. Powder compositions of arginine bicarbonate/calcium carbonate provided in slurries or pastes are suitable for the formation of tubule plugs and use as a cavity lining material. Since dentinal fluid is derived from pulpal fluid, the arginine bicarbonate/calcium carbonate composition can provide the exposed pulp with a capping at the same time that adjacent open tubules are plugged.

A related application is the calcification or mineralization of pits and fissures, which are sites where oral stimuli have access to underlying dentinal tubules because the enamel at their bases or sides is breeched as a result of tooth formation deficiencies or because of dental caries. Here, one can scoop or clean out the organic material in the pit or fissure with mechanical devices, and add arginine bicarbonate/calcium carbonate composition before placing a dental sealant or other filling thereon.

Cavities deep enough to reach dentine exhibit sensitivity because they often involve open dentinal tubules. Inserting powder or paste compositions into carious lesions plugs these tubules and at the same time calcifies, hardens, and seals off difficult to remove carious material, a related application of this invention. Calcification of exposed tooth pulps can also be accomplished. Like dentinal fluid, pulp fluid (which is the source of dentinal fluid) contains calcium and phosphate so that it is amenable to calcification and sealing off the pulp from the oral environment. Once more, because of the alkaline pH and calcium provided, a slurry or paste containing arginine bicarbonate/calcium carbonate to an exposed pulp will suffice. This can also be placed into a pulp chamber from which pulp tissue has been removed.

In order to further illustrate the present invention, experiments described in the following examples were carried out. It should be understood that the invention is not limited to the specific examples or the details described therein.

EXAMPLE 1

Conditions for Intrinsic Plug Formation

None of the prior art methods described above have used compositions that stimulate intrinsic blockage of the dentinal tubule. In this case, formation of a deposit uses tubule contents. Being a tissue fluid, dentinal fluid contains calcium and phosphate ions, which makes it amenable to calcification.

Figure 2:
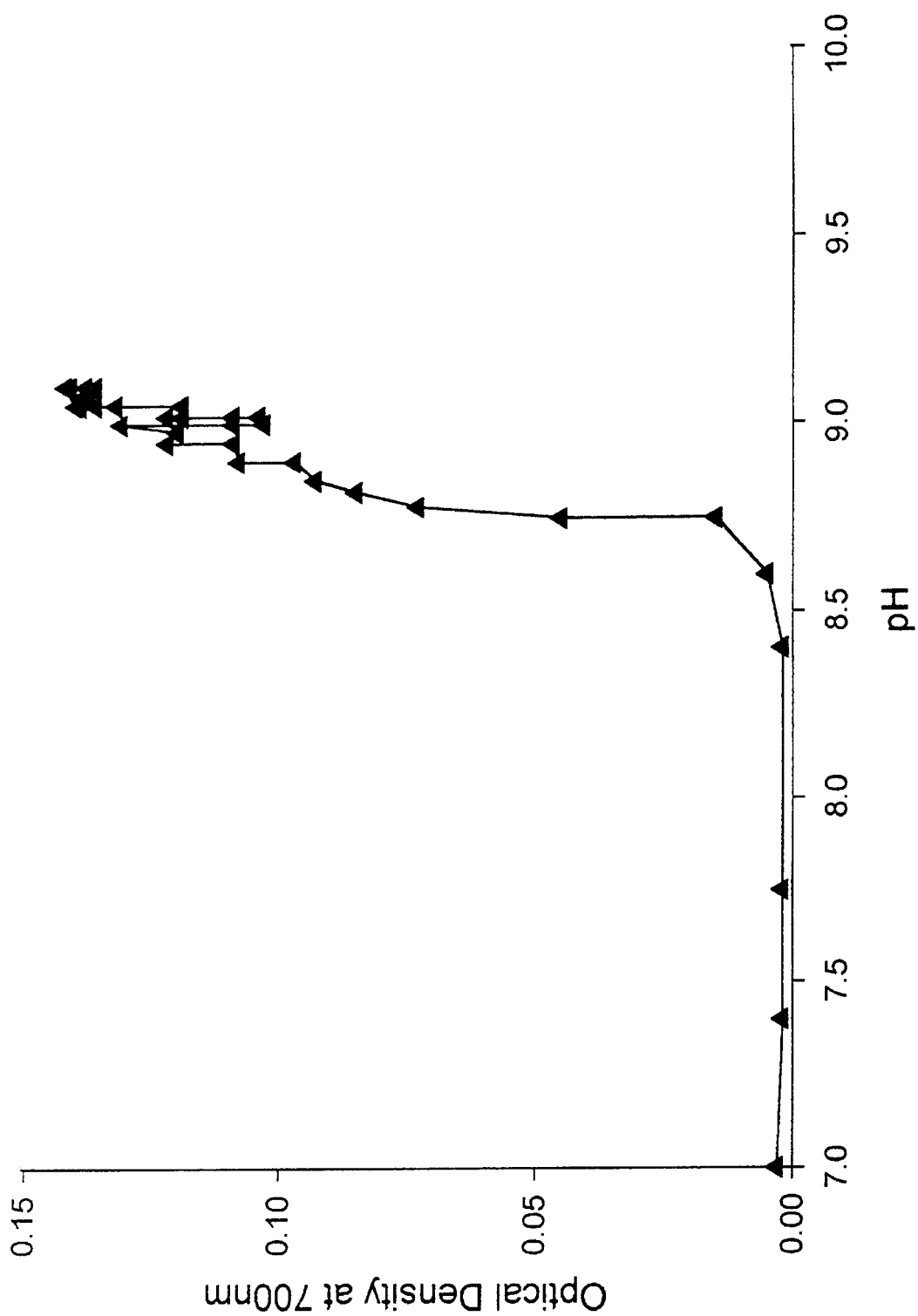
FIG. 2. Titration of artificial dentinal fluid with the supernatant of an arginine bicarbonate/calcium carbonate powder suspension.
Figure 3:
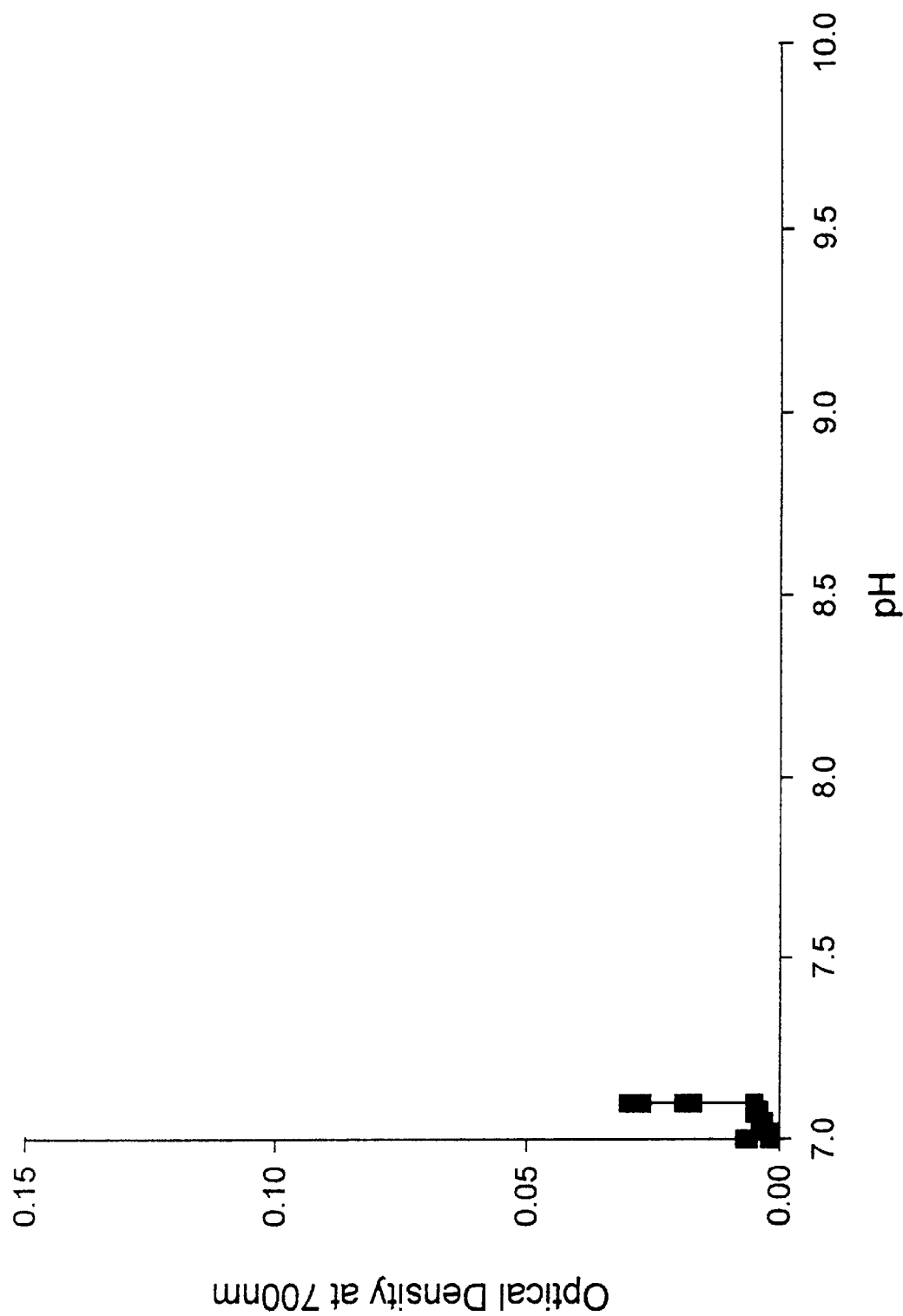
FIG. 3. Titration of artificial dentinal fluid with the supernatant of a calcium carbonate ($CaCO_3$) suspension.
Figure 4:
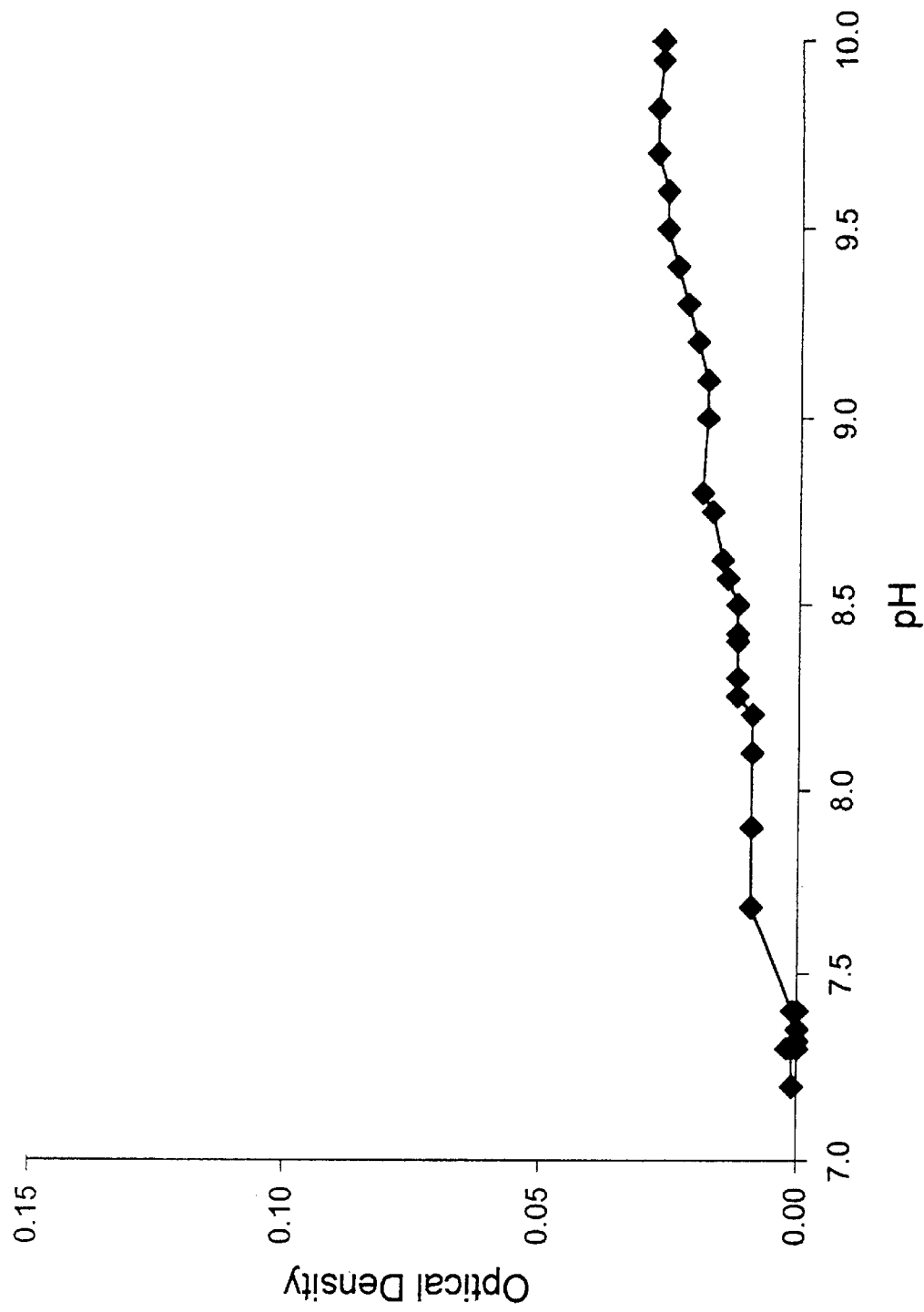
FIG. 4. Titration of artificial dentinal fluid with sodium hydroxide (NaOH) solution.

In order to determine the conditions that promote intrinsic plug formation, we performed the following experiments. We prepared a solution comprised of the ions present in dentinal fluid (which acted as artificial dentinal fluid) and progressively added (titrated) various solutions thereto to determine the conditions and substances conducive to the formation of aggregates (i.e., dentinal plugs). Aggregation was determined by means of measurement of the absorbance with a spectrophotometer. From this, it was clear that at a pH of 8.5 and above, aggregation of dentinal fluid constituents occurred with arginine bicarbonate (FIG. 1), and was enhanced by the addition of calcium carbonate (FIG. 2). Calcium carbonate by itself was not sufficient to produce deposit formation (FIG. 3), nor could one induce deposition by elevation of the pH as with addition of sodium hydroxide (FIG. 4) or sodium bicarbonate. Desirable precipitation was achieved by simultaneously raising the pH with highly soluble arginine bicarbonate and providing calcium from poorly soluble calcium carbonate (to supplement the calcium in dentinal tubule fluid), which calcium carbonate also acted as a filler material as described above to increase the ability to achieve tubule plugging. The 2 to 5 $\mu$m particle size of the calcium carbonate was small enough to easily enter the dentinal tubules and reduce the amount of precipitate needed to produce a stronger and more complete plug.

A composition of arginine bicarbonate, which is highly soluble, with poorly soluble calcium carbonate yielded a pH between about 8.5 and about 9.0, which is highly favorable for tubule plugging.

EXAMPLE 2

In vivo Model of Tubule Plugging

A device developed by Greenhill and Pashley (J. Dental Research, 60:686–698, 1981) that enables simulation of dentinal tubule plugging in vivo was used to assess the effectiveness of the invention. Dentine discs that varied in thickness from 0.6 to 0.8 mm were cut with a Buhler Isomet saw from extracted caries-free molar teeth. They were then etched with 6% citric acid for two minutes to remove the smear layer and stored in 70% ethanol until used. A disc was mounted in the chamber of the apparatus with occlusal side facing upwards. The occlusal side is determined by passing light through a plastic grid beneath the section and observing the section with a dissecting microscope. The tubules appear further apart with the occlusal side up because of the lower tubular density of the dentine occlusally (Walton et al., J. Dental Research 55:639–642, 1976). Hydraulic conductance of fluid through the discs was determined as described by Greenhill and Pashley, supra.

Fluid containing levels of ions present in serum (Merck Manual, 1972) was used to perfuse the disc. Their concentrations in mM were as follows: Na-140.5, K-4.31, Ca-2.5, Mg-1.0, P-1.3. The pH of this solution is raised to 7.0 with sodium hydroxide. The solution was filtered through a 0.22 mm filter (Millipore Corp., Marlborough, Mass. 01752) prior to use to remove any bacteria present. This solution is called artificial ionic dentinal fluid (AIDF). Hydrostatic pressure was created by a fluid reservoir leading via a glass capillary tube into the pulpal side of the chamber at a level 30 cm above that of the surface of the horizontally positioned disc. The distance traveled by an air bubble positioned in the AIFD in the capillary tubing between this pressure head and the pulpal side of the disc in a fixed period of time was converted to hydraulic conductance values in ml $cm^{-1}$ $min^{-1}$ cm $H_2O^{-1}$.

Sections were exposed to an arginine bicarbonate/calcium carbonate mixture and various controls as follows. First, 400 ml of AIDF was applied to the upward facing occlusal side of the section and AIDF was allowed to flow through the disc from the pulpal side for a period of five minutes. The distance that the air bubble moved inside the capillary on the pulpal side of the chamber was measured so that the rate of fluid movement through the disc could be calculated and converted to hydraulic conductance values. This procedure was repeated two more times or until a uniform flow rate was achieved on three consecutive runs. The AIDF was then replaced by 400 $\mu$l of a 1:4 arginine bicarbonate/calcium carbonate slurry and brushed on the dentine surface for two minutes. Next, the mixture was removed with a pipette, washed three times with 400 $\mu$l of deionized water and replaced with AIDF. The AIDF was allowed to flow through the dentine slice and hydraulic conductance readings were made at selected times up to 90 minutes.

New dentin sections were selected and the experiment repeated using either (i) sodium bicarbonate plus calcium carbonate in the same ratio as the arginine bicarbonate/calcium carbonate mixture, (ii) arginine bicarbonate alone, (iii) sodium bicarbonate (iv) calcium carbonate alone, or (v) distilled water.

Table 1 shows the results. The hydraulic conductance fell the most with the arginine bicarbonate/calcium carbonate mixture. Calcium carbonate, arginine bicarbonate, distilled water and combining sodium bicarbonate and calcium carbonate had much smaller effects, in some cases, a negative result (i.e. an increase in conductance) was seen. Examination of the discs by scanning electron microscopy revealed substantial blockage of the orifices of the dentinal tubules with the arginine bicarbonate/calcium carbonate mixture but little or no blockage with the other test substances shown in the table. Blockage of dentinal tubules is considered central to reduction of dentinal hypersensitivity.

TABLE 1

Percent Reduction in Hydraulic Conductance

| Test Compounds | Minutes after exposure | | | | | | |
|---|---|---|---|---|---|---|---|
| | 0 | 15 | 30 | 45 | 60 | 75 | 90 |
| arginine bicarbonate + calcium carbonate | 0 | 13.7 | 23.3 | 28.1 | 30.8 | 34.9 | 35.6 |
| sodium bicarbonate + calcium carbonate | 0 | −36.1 | −27.8 | −31.3 | −34.0 | −31.3 | −28.5 |
| arginine bicarbonate | 0 | 11.7 | 15.6 | 14.4 | 14.5 | 16.1 | 16.1 |
| sodium bicarbonate | 0 | −10.6 | −1.0 | 7.2 | 11.5 | 15.9 | 19.7 |
| calcium carbonate | 0 | −18.5 | −12.3 | −5.5 | −4.1 | 5.5 | 5.5 |
| water | 0 | 2.0 | 1.0 | 5.6 | 8.1 | 8.1 | 8.1 |

EXAMPLE 3

Adhesive Properties of the Plugging Composition

Arginine bicarbonate has adhesive properties desirable for plugging dentinal tubules. Arginine bicarbonate is prepared from arginine (free base) by titrating the arginine with gaseous carbon dioxide as follows. 7.5 g of arginine is dissolved in 50 ml of deionized water and has a pH of about 10.6. Then carbon dioxide is delivered thereto under pressure (2 lbs./sq. in.) from a commercial gas cylinder until a solution pH of 7.2 is reached. This is the pH at which the carbon dioxide has converted all or most of the arginine to arginine bicarbonate. For intrinsic plugging and the formation of salivary precipitin, a pH between 8 and 9 is preferred. This is done by titrating the arginine with carbon dioxide to a desired pH between 8 and 9 or by mixing of the arginine bicarbonate with the more alkaline arginine free base to a desired pH between 8 and 9. The adhesive properties of arginine bicarbonate are retained as well as the ability to produce intrinsic plugging and promotion of salivary precipitin formation.

Figure 5A:
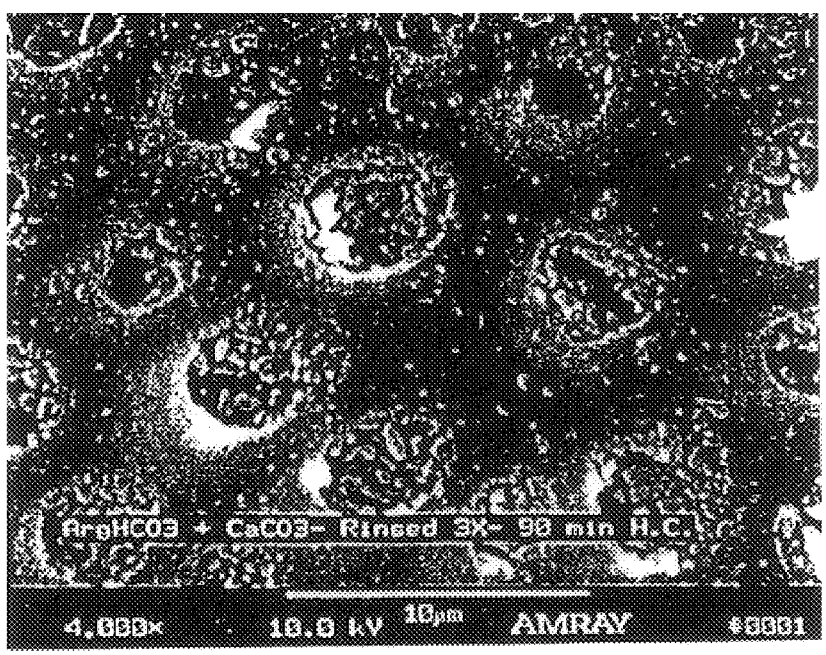
FIGS. 5A and 5B. Scanning electron photomicrograph showing (A) dentinal tubules after exposure to arginine bicarbonate/calcium carbonate powder suspension, and (B) control prior to exposure.
Figure 5B:
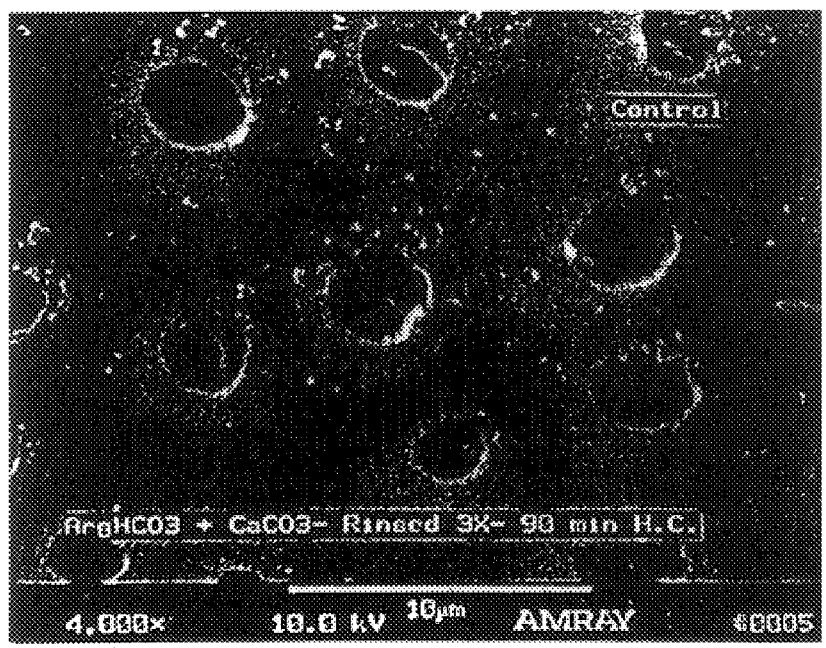
Figure 6A:
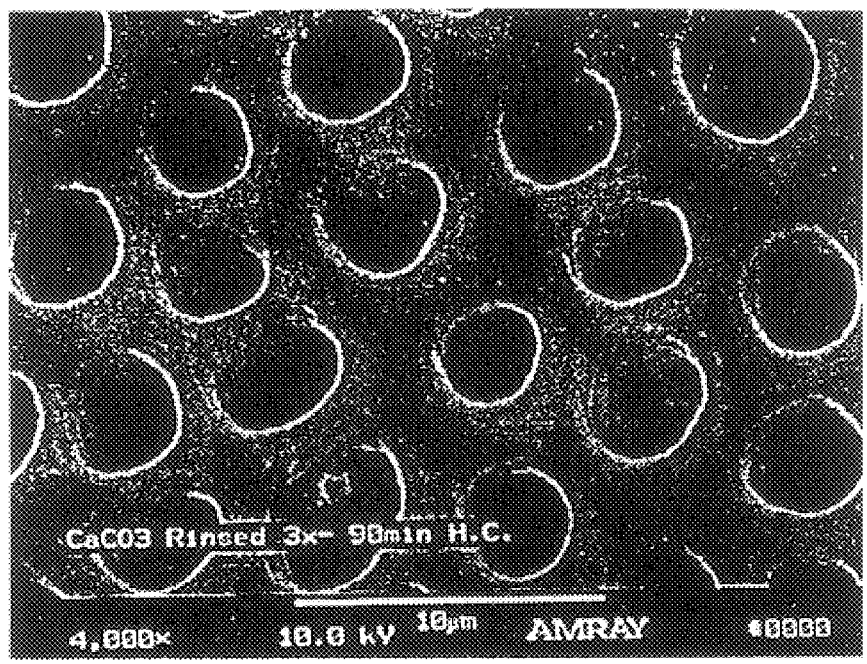
FIGS. 6A and 6B. Scanning electron photomicrograph showing (A) dentinal tubules after exposure to calcium carbonate powder suspension, and (B) control prior to exposure.
Figure 6B:
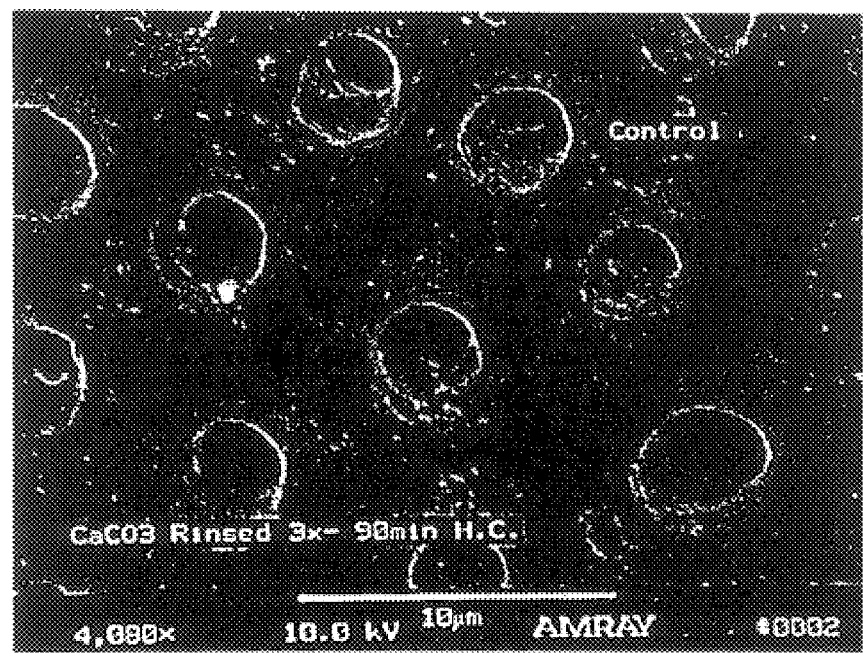
Figure 7A:
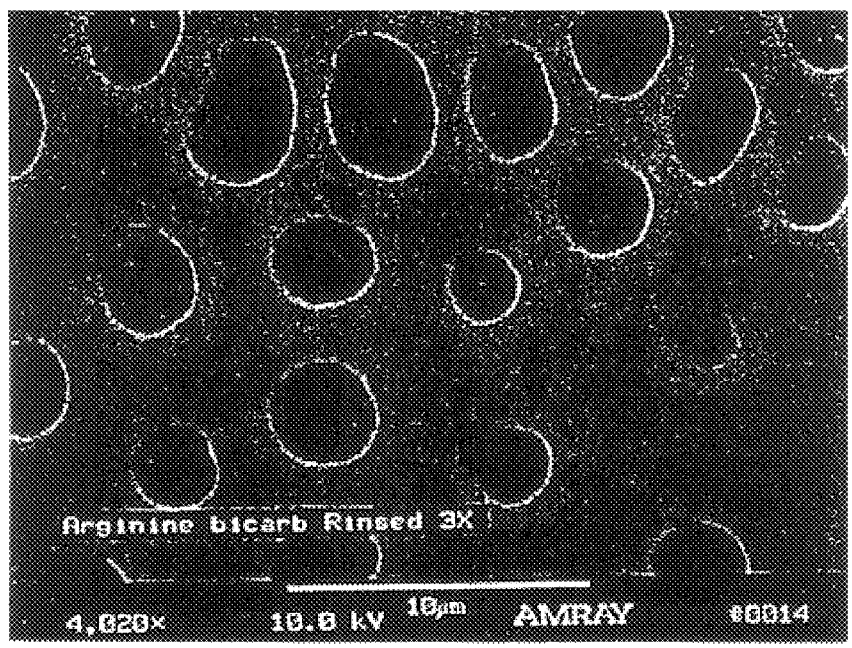
FIGS. 7A and 7B. Scanning electron photomicrograph showing (A) dentinal tubules after exposure to arginine bicarbonate, and (B) control prior to exposure.
Figure 7B:
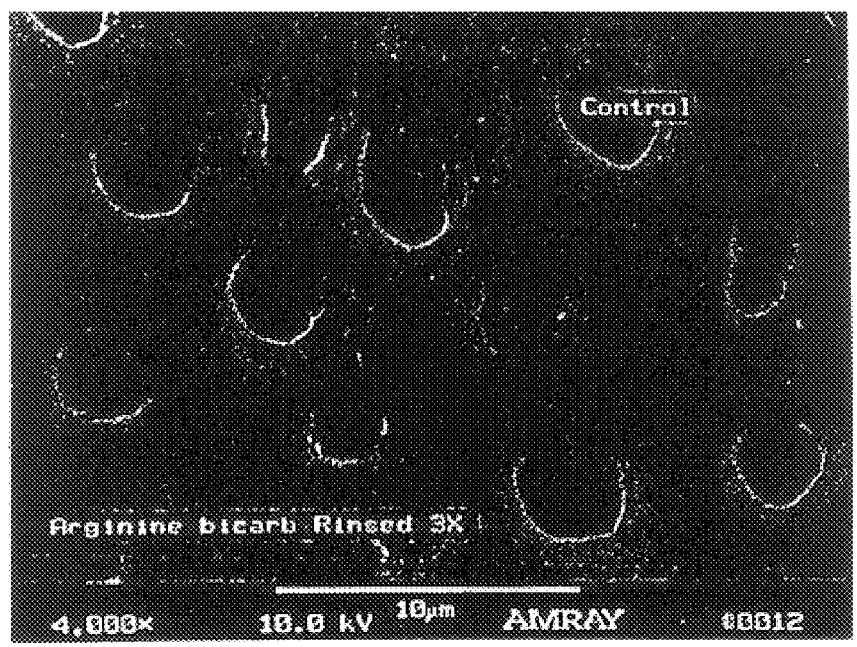

Scanning electron micrographs show the ability of arginine bicarbonate plus calcium carbonate to plug open dentinal tubules (FIG. 5A) compared to calcium carbonate alone (FIG. 6A) and arginine bicarbonate alone (FIG. 7A). Control samples (FIGS. 5B, 6B, 7B) were photographed prior to exposure to arginine bicarbonate plus calcium carbonate or either compound alone. Thus, although calcium carbonate is a poorly soluble calcium salt, its small particle size and interaction with arginine bicarbonate make the combination suitable for plugging open dentinal tubules.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

All patents, patent applications, publications, and other materials cited herein are hereby incorporated herein reference in their entireties.

What is claimed is:

1. An oral composition comprising a guanidinium alkaline salt or free base, a calcium salt which is poorly soluble in water, and an orally acceptable carrier, wherein the pH of the composition ranges from about 7.5 to about 9.5.

2. The composition of claim 1, wherein the guanidinium is arginine.

3. The composition of claim 2, wherein the arginine salt is selected from the group consisting of arginine bicarbonate, arginine hydroxide, arginine carbonate, arginine phosphate, and arginine organic phosphate.

4. The composition of claim 1, wherein the solubility of the calcium salt is between about 0.1 and about 100 mg in 100 ml of water near and about room temperature and near and above pH of about 5.

5. The composition of claim 1, wherein the calcium salt is selected from the group consisting of calcium carbonate, monocalcium phosphate, dicalcium phosphate, tricalcium phosphate, calcium fluoride, calcium monofluorophosphate, sodium calcium pyrophosphate, calcium laurate, calcium palmitate, and combinations thereof.

6. The composition of claim 1, further comprising a protein denaturing agent.

7. The composition according to claim 1, wherein the oral composition is selected from the group consisting of a dental care product, a food product, and chewing gum.

8. The composition of claim 1 wherein the pH ranges from about 8.0 to about 9.0.

9. A composition comprising an arginine salt and calcium carbonate which is poorly soluble in water, wherein the pH of the composition ranges from about 7.5 to about 9.5 in an aqueous slurry or paste.

10. The composition according to claim 9, wherein the aqueous slurry is isotonic.

11. The composition of claim 9 wherein the pH ranges from about 8.0 to 9.0.

12. A powder composition comprising an arginine salt and calcium carbonate which is poorly soluble in water, wherein the pH of the composition ranges from about 7.5 to about 9.5 when in contact with a calcium phosphate solution or slurry, dentinal tubule fluid, saliva, dentinal pulp, or pupal fluid.

13. The composition of claim 12 wherein the pH ranges from about 8.0 to 9.0.

14. A pulpal calcification filling comprising an arginine salt and calcium carbonate which is poorly soluble in water, and a filling carrier wherein the pH of the composition ranges from about 7.5 to about 9.5.

15. The composition of claim 14, wherein the carrier is selected from the group consisting of saline, zinc oxide-eugenol, and carboxymethylcellulose-ethyl alcohol.

16. The composition of claim 14 wherein the pH ranges from about 8.0 to 9.0.

* * * * *